US00PP13230P2

(12) United States Plant Patent
Hanes

(10) Patent No.: US PP13,230 P2
(45) Date of Patent: Nov. 12, 2002

(54) GERANIUM PLANT NAMED 'FREELIGHT LAV TWO'

(75) Inventor: Mitchell Eugene Hanes, Morgan Hill, CA (US)

(73) Assignee: Goldsmith Plants, Inc., Gilroy, CA (US)

( * ) Notice: Subject to any disclaimer, the term of this patent is extended or adjusted under 35 U.S.C. 154(b) by 39 days.

(21) Appl. No.: 09/921,795

(22) Filed: Aug. 6, 2001

(51) Int. Cl.[7] ..... A01H 5/00
(52) U.S. Cl. ..... Plt./332
(58) Field of Search ..... Plt./332

*Primary Examiner*—Kent L. Bell
(74) *Attorney, Agent, or Firm*—Rothwell, Figg, Ernst & Manbeck

(57) ABSTRACT

A geranium cultivar particularly distinguished by green foliage, lavender flower color, and double flowers on large umbels, fast rooting and exhibits vigorous growth.

2 Drawing Sheets

GENUS AND SPECIES

*Pelargonium peltatum.*

VARIETY DENOMINATION

'Freelight Lav Two'.

BACKGROUND OF THE NEW PLANT

The present invention comprises a new and distinct cultivar of geranium, botanically known as *Pelargonium peltatum*, and hereinafter referred to by the cultivar name 'Freelight Lav Two'. The new cultivar originated from a cross made by the inventor of the seed parent, an unnamed, unpatented, light lavender semi-double flowered plant from proprietary breeding line 7161-1 and an unnamed, unpatented, white flowered plant from proprietary breeding line 7290-1.

'Freelight Lav Two' is a product of a planned breeding program intended to creat new geranium cultivars with lavender colored flowers, semi-double flower form, dark green foliage, vigorous growth and superior cutting productivity.

The new cultivar was created in 1997 in Gilroy, Calif. and has been asexually reproduced repeatedly by cuttings in Gilroy, Calif. over a two year period. The plant has also been trialed at Gilroy, Calif. and Andijk, The Netherlands. The plant has been found to retain its distinctive characteristics through successive propagations; and this novelty is firmly fixed.

DESCRIPTION OF PHOTOGRAPH

The new geranium plant is illustrated by the accompanying photographs which show blooms, buds, and foliage of the plant in full color, the colors shown being as true as can be reasonably obtained by conventional photographic procedures.

DESCRIPTION OF THE NEW CULTIVAR

Figure 1:
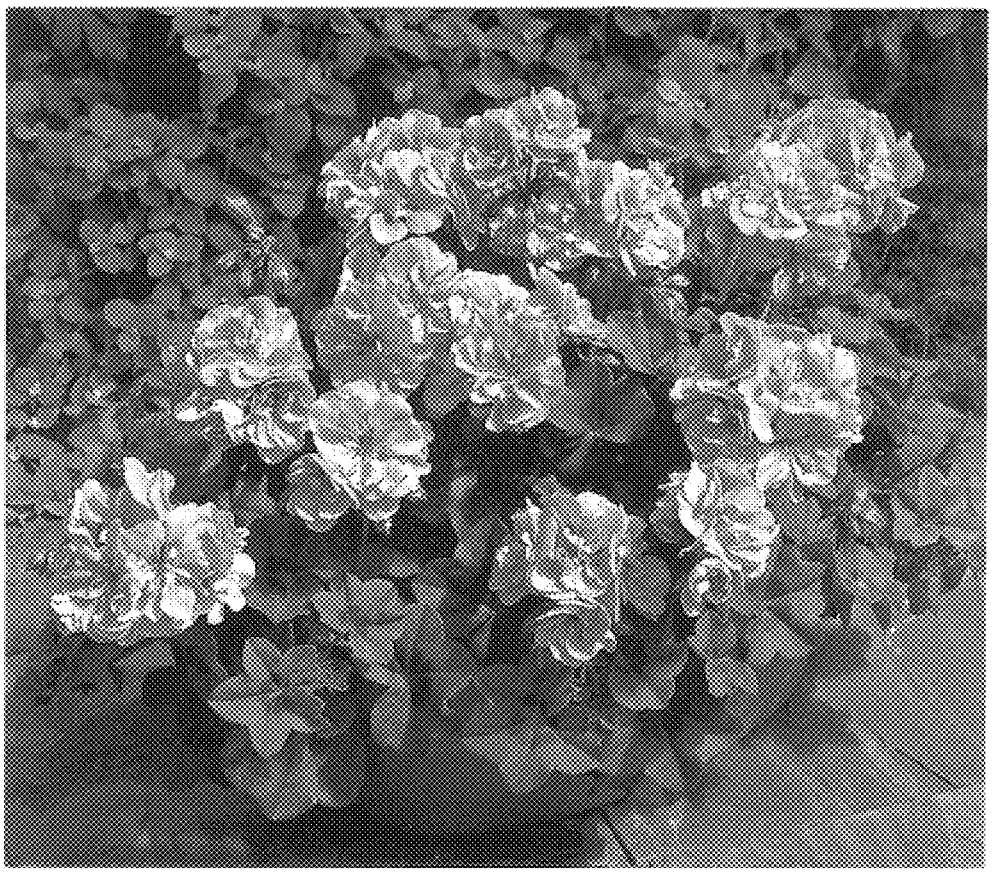
FIG. 1 shows overall plant habit.
Figure 2:
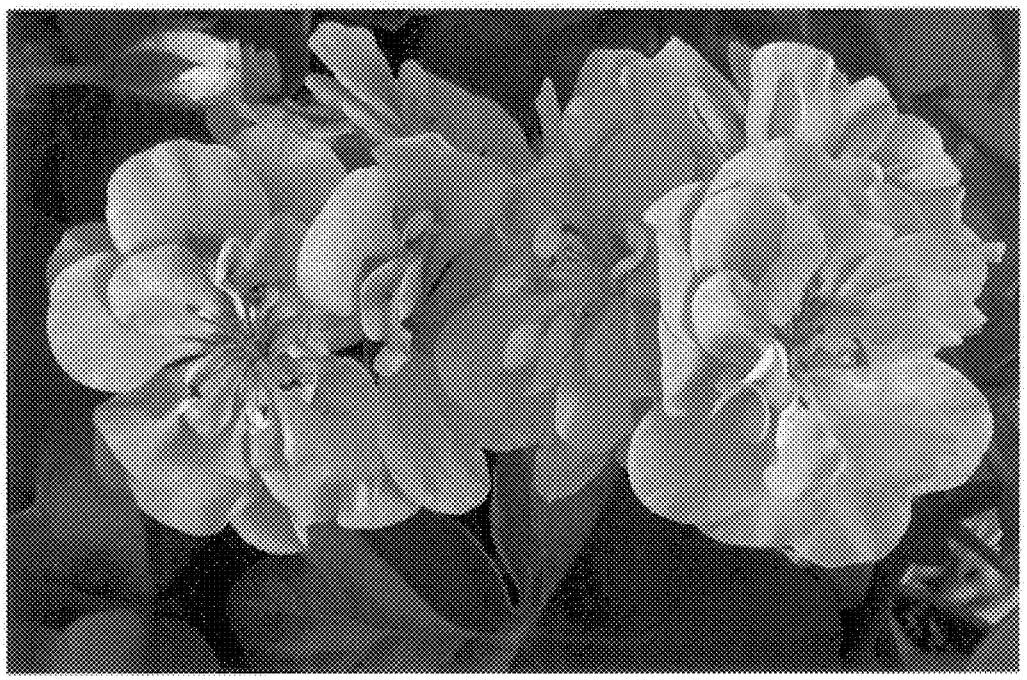
FIG. 2 shows mature inflorescences.

The following detailed descriptions set forth the distinctive characteristics of 'Freelight Lav Two'. The data which defines these characteristics were collected from asexual reproductions carried out in Gilroy, Calif. The plant history was taken on seven month old plants grown in 8 inch pots, blossomed under natural light in a greenhouse and color readings were taken in the greenhouse in Gilroy, Calif. Color references are primarily to The R.H.S. Colour Chart of The Royal Horticultural Society of London (R.H.S.).

DETAILED BOTANICAL DESCRIPTION

Classification:
*Botanical.*—*Pelargonium peltatum.*
*Commercial.*—Ivy Geranium.
Form: Upright, spreading.
Height:
*From soil level to top of plant* (*excluding blooms*).—15–19 cm.
*From soil level to top of umbels.*—29 cm.
Width: 40 cm; if lateral branches are outstretched the width is 50 cm.
Time to produce a finished flowering plant: 13 weeks.
Outdoor plant performance: Good weather tolerance; strong growth.
Time to initiate roots: 8–10 days.
Time to develop roots: 26–28 days.
Root description: White, slightly pubescent, fibrous yet coarse.

THE LEAVES

Length: 5.6–6.0 cm.
Width: 6.0 cm.
Apex description: Cuspidate.
Base description: Cordate.
Shape: Reniform, five lobed, apex of lobes are cuspidate.
Margin: Entire, ciliate.
Textue: Smooth, glabrous.
Ribs and veins: Palmate, 3.5–4.0 cm long.
Color:
*Upper side.*—Green RHS 146B.
*Under side.*—Green RHS 146C.
*Ribs and veins.*—A green color between RHS 144B and 144C.
Zonation: 2.5–3.0 cm wide of brown RHS 200A to 200C (the 5 mm in the center of the zone are green 146B). The zone color varies between RHS 200A and 200C on certain leaves that have not been exposed to as much sunlight. In lower light levels and with excessive lush growth, the zone is not visible.

Petiole length: 5.0–9.0 cm depending on age of the leaf.
Petiole diameter: 2.0 mm.
Petiole color: Between Yellow-green RHS 144A and Yellow-green RHS 144B.
Lateral branch length: 10–25 cm.
Internode length: 2.0–4.0 cm.
Lateral branch color: Yellow-green RHS 144B.

THE BUD

Diameter: 8.0 mm.
Length: 1.7 cm.
Shape: Ovate.
Color when sepals first divide: Purple RHS 75C.
Number of sepals: Five, pubescent with long white hairs.
Length of sepals: 1.5 cm.
Width of sepals: 3.0–5.0 mm.
Apex description: Acuminate/aristate.
Base description: Truncate.
Sepal color in an open flower: Upper and lower surfaces are green RHS 144B.

THE FLOWER

Size: Approximately 5.5 cm in diameter.
Form: Double, polypetalous corolla.
Petals/petaloids: 15–16 petals, 6–7 petaloids; Shape: spatulate.
Apex shape: Obtuse/retuse.
Base shape: Attenuate.
Margin: Entire.
Upper petal/petaloid color:

*Petal upper surface.*—Violet RHS 84B with a (5 mm×3 mm with irregular edges) macule of purple RHS 74A and (1.3 cm×less than 1 mm) stripe of purple 74A.

*Petal under surface.*—Purple RHS 75C with stripes (approximately 1.5–2.0 cm long) of purple RHS 74B.

*Petaloid upper and under surface.*—Violet RHS 84B.

Lower petal/petaloid color:

*Petal upper surface.*—Violet RHS 84B; purple RHS 75C on under surface.

*Petaloid upper and under surface.*—Violet RHS 84B.

Color change with age: Colors do not change with age.
Pedicel length: Approximately 2.2–2.5 cm.
Pedicel color: Yellow-green RHS 144B.
Flower persistence: An open flower will hold its petals until the flower begins to dehisce, or approximately 7–10 days.

THE INFLORESCENCE

Type: An umbel composed of approximately 6–9 flowers.
Diameter: 8.0–9.0 cm.
Depth: 5.0 cm.
Peduncle length: 8.5–10.0 cm.
Peduncle color: Yellow-green RHS 144B.

THE REPRODUCTIVE ORGANS

Anthers: 8
Anther color: Pink RHS 68A.
Filament color: Base is white RHS 155A and top (closest to anther) is pink RHS 68A.
Pollen amount and color: Moderate, orange RHS 25A.
Pistil: 1 with a length of 8 mm–1 cm.
Stigma: 6 linear lobes with a color of pink RHS 67A.
Stigma: 4.0 mm in length with a color of pink RHS 54D.
Ovary: At anthesis, densely pubescent with white hairs, oblong, green drying to a light brown at maturity.
Seed number: Maximum of 5 per spike.
Seed length: 4–5 mm.
Seed width: 1.0–1.5 mm.
Seed color: Grey-orange RHS 177B that may darken with age.

DISEASE AND INSECT RESISTANCE

No susceptibility to diseases or insects noted to date.

COMPARISON WITH KNOWN CULTIVARS

When the instant plant is compared to the seed parental cultivar, an unnamed, unpatented plant form proprietary breeding line 7161-1, 'Freelight Lav Two' has a more branched, spreading habit. When 'Freelight Lav Two' is compared to the pollen parental cultivar, an unnamed, unpatented plant from proprietary breeding line 7290-1, the instant plant is lavender flowered and has a more vigorous, branched habit versus the white, compact, small-leafed parental plant.

I claim:

1. A new and distinct cultivar of geranium plant as shown and described herein.

* * * * *